(12) United States Patent
Malven et al.

(10) Patent No.: US 8,053,184 B2
(45) Date of Patent: Nov. 8, 2011

(54) SOYBEAN EVENT MON89788 AND METHODS FOR DETECTION THEREOF

(75) Inventors: Marianne Malven, Ellisville, MO (US); Jennifer Rinehart, Spring Green, WI (US); Nancy Taylor, Chesterfield, MO (US); Ellen Dickinson, Kirkwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/575,352

(22) Filed: Oct. 7, 2009

(65) Prior Publication Data

US 2010/0099859 A1    Apr. 22, 2010

Related U.S. Application Data

(62) Division of application No. 11/441,914, filed on May 26, 2006, now Pat. No. 7,632,985.

(60) Provisional application No. 60/685,584, filed on May 27, 2005.

(51) Int. Cl.
C12Q 1/68      (2006.01)
C12P 19/34     (2006.01)
C07H 21/04     (2006.01)

(52) U.S. Cl. ........ 435/6; 435/91.2; 536/22.1; 536/24.33

(58) Field of Classification Search ................. 435/91.2, 435/6; 536/22.1, 24.33
See application file for complete search history.

(56) References Cited

U.S. PATENT DOCUMENTS

| | | | |
|---|---|---|---|
| 2,627,469 A | 2/1953 | Melnick et al. ............... 426/605 |
| 4,144,229 A | 3/1979 | Karnofsky .................... 530/378 |
| 4,535,060 A | 8/1985 | Comai ...................... 435/172.3 |
| 5,094,945 A | 3/1992 | Comai ...................... 435/172.3 |
| 5,110,805 A | 5/1992 | Berner et al. ................... 514/76 |
| 5,188,642 A | 2/1993 | Shah et al. ...................... 47/58 |
| 5,310,667 A | 5/1994 | Eichholtz et al. ............ 435/91.1 |
| 5,312,910 A | 5/1994 | Kishore et al. ............... 536/23.2 |
| 5,437,697 A | 8/1995 | Sebastian et al. ................. 47/58 |
| 5,463,175 A | 10/1995 | Barry et al. .................... 800/300 |
| 5,554,798 A | 9/1996 | Lundquist et al. ......... 800/300.1 |
| 5,627,061 A | 5/1997 | Barry et al. .................... 800/288 |
| 5,633,435 A | 5/1997 | Barry et al. .................... 800/288 |
| 5,659,114 A | 8/1997 | Paschall, II ................... 800/312 |
| 5,804,425 A | 9/1998 | Barry et al. .................... 435/193 |
| 5,824,877 A | 10/1998 | Hinchee et al. ............... 800/205 |
| 6,040,497 A | 3/2000 | Spencer et al. ............... 800/288 |
| 6,080,916 A | 6/2000 | Holmes ......................... 800/312 |
| 6,248,876 B1 | 6/2001 | Barry et al. ................... 536/24.3 |
| 6,384,301 B1 | 5/2002 | Martinell et al. ............. 800/294 |
| 6,462,258 B1 | 10/2002 | Fincher et al. ................ 800/300 |
| 6,573,425 B1 | 6/2003 | Baszczynski et al. ........ 800/278 |
| 6,610,910 B1 | 8/2003 | Streit et al. .................... 800/312 |
| 6,660,911 B2 | 12/2003 | Fincher et al. ................ 800/300 |
| 6,689,880 B2 | 2/2004 | Chen et al. ................... 536/24.3 |
| 6,733,974 B1 | 5/2004 | Feazel ............................... 435/6 |
| 6,740,488 B2 | 5/2004 | Rangwala et al. ................ 435/6 |
| 6,818,807 B2 | 11/2004 | Trolinder et al. ............. 800/300 |
| 6,825,400 B2 | 11/2004 | Behr et al. .................. 800/300.1 |
| 6,893,826 B1 | 5/2005 | Hillyard et al. ................... 435/6 |
| 6,900,014 B1 | 5/2005 | Weston et al. ................... 435/6 |
| 6,919,495 B2 | 7/2005 | Fincher et al. ............... 536/23.2 |
| 6,984,774 B1 | 1/2006 | Peterson et al. .............. 800/278 |
| 7,098,170 B2 | 8/2006 | Asrar et al. ................... 504/272 |
| 7,164,056 B2 | 1/2007 | Lyznik et al. ................. 800/278 |
| 7,183,110 B2 | 2/2007 | Barry et al. .................... 435/816 |
| 7,306,909 B2 | 12/2007 | Krieb et al. ......................... 435/6 |
| 7,405,074 B2 | 7/2008 | Castle et al. ................... 800/300 |
| 7,405,347 B2 | 7/2008 | Hammer et al. .............. 800/278 |
| 7,504,561 B2 | 3/2009 | Hammer et al. .............. 800/300 |
| 7,538,262 B2 | 5/2009 | Hammer et al. .............. 800/300 |
| 7,608,761 B2 | 10/2009 | Baley et al. .................... 800/300 |
| 2002/0133852 A1 | 9/2002 | Hauge et al. ..................... 702/19 |
| 2003/0083480 A1 | 5/2003 | Castle et al. .................. 536/23.1 |
| 2003/0114308 A1 | 6/2003 | De Billot ....................... 504/100 |
| 2005/0223425 A1 | 10/2005 | Clinton et al. .............. 504/116.1 |
| 2005/0233905 A1 | 10/2005 | DeBillot et al. .............. 504/102 |
| 2006/0111239 A1 | 5/2006 | Oakley et al. ............... 504/116.1 |
| 2006/0223707 A1 | 10/2006 | Baley et al. .................... 504/100 |
| 2006/0282911 A1 | 12/2006 | Bull et al. ...................... 800/267 |
| 2007/0083945 A1* | 4/2007 | Byrum et al. .................. 800/278 |
| 2007/0197474 A1 | 8/2007 | Clinton et al. ................ 504/206 |
| 2007/0277267 A1* | 11/2007 | Byrum ........................... 800/285 |

FOREIGN PATENT DOCUMENTS

| | | |
|---|---|---|
| DE | 100 59 609 | 6/2002 |
| WO | WO 92/00377 | 1/1992 |
| WO | WO 99/23232 | 5/1999 |
| WO | 99/51759 A1 | 10/1999 |
| WO | WO 99/51759 | 10/1999 |
| WO | WO 01/44457 | 6/2001 |
| WO | WO 01/44457 A2 | 6/2001 |
| WO | WO 01/49104 | 7/2001 |
| WO | WO 02/06500 | 1/2002 |
| WO | WO 02/14521 | 2/2002 |

(Continued)

OTHER PUBLICATIONS

The nucleic acid sequences search reports for SEQ ID Nos. 3 and 4.*
Catalog stratagene, 1988.*
U.S. Appl. No. 60/685,584, filed May 27, 2005, Eathington.
Agbios Database, Event MON-04032-6 (GTS 40-3-2), undated.
Agbios Database, Event MON-89788-1 (MON89788), undated.
Anderson et al., "Rust control in glyphosate tolerant wheat following application of the herbicide glyphosate," *Plant Disease*, 89(11):1136-1142, 2005.

(Continued)

*Primary Examiner* — Kenneth R. Horlick
*Assistant Examiner* — Joyce Tung
(74) *Attorney, Agent, or Firm* — SNR Denton US LLP; Pamela J. Sisson, Esq.

(57) ABSTRACT

The present invention provides for soybean plant and seed comprising transformation event MON89788 and DNA molecules unique to these events. The invention also provides methods for detecting the presence of these DNA molecules in a sample.

10 Claims, 3 Drawing Sheets

FOREIGN PATENT DOCUMENTS

| | | |
|---|---|---|
| WO | WO 02/44407 | 6/2002 |
| WO | WO 03/013224 | 2/2003 |
| WO | WO 2004/006659 A1 | 1/2004 |
| WO | WO 2004/043150 | 5/2004 |
| WO | WO 2004/070020 | 8/2004 |
| WO | WO 2004/072235 | 8/2004 |
| WO | WO 2004/074492 | 9/2004 |
| WO | WO 2004/074492 A1 | 9/2004 |
| WO | WO 2005/041669 | 5/2005 |
| WO | WO 2005/102057 | 11/2005 |
| WO | WO 2006/130436 | 12/2006 |
| WO | WO 2007/017256 | 2/2007 |

OTHER PUBLICATIONS

Axelos et al., "The gene family encoding the *Arabidopsis thaliana* translation elongation factor EF-1 alpha: molecular cloning, characterization and expression," *Mol. Gen Genet*, 219(1-2):106-112, 1989.

Barker et al., "Nucleotide sequence of the T-DNA region from the *Agobacterium tumefaciens* octopine Ti plasmid pTi15955," *Plant Mol. Biol.*, 2:335-350, 1983.

Chevalier et al., "Design, activity, and structure of a highly specific artificial endonuclease," *Molecular Cell*, 10:895-905, 2002.

Coruzzi et al., "Tissue-specific and light-regulated expression of pea nuclear gene encoding the small subunit of ribulos-1,5-bisphosphate caroxylase," *EMBO J.*, 3:1671-1679, 1984.

Depicker et al., "Nopaline synthase: transcript mapping and DNA sequence," *J. Mol. Appl. Genet*, 1(6):561-573, 1982.

Feng et al., "Glyphosate inhibits rust diseases in glyphosate-resistant wheat and soybean," *PNAS*, 102(48):17290-17295, 2005.

Franz et al., "Glyphosate: a unique global herbicide," *American Chemical Society*, Chapter 5:103-141, 1997.

Grossbard, "Effects of glyphosate on the microflora: with reference to the decomposition of treated vegetation and interaction with some plant pathogens," Chapter 11 in The Herbicide Glyphosate, Grossbard et al. ed., 159-165, 178-182, 1985.

Harrison et al., "The expressed protein in glyphosate-tolerant soybean, 5-enolpyruvylshikimate-3-phosphate synthase from *Agrobacterium* sp. strain CP4, is rapidly digested in vitro and is not toxic to acutely gavaged mice,"*J. Nutr.*, 126(3):728-740, 1996.

Hernandez et al., "Development of melting temperature-based SYBR green I polymerase chain reaction methods for multiplex genetically modified organism detection," *Analytical Biochemistry*, 323(2):164-170, 2003.

Hofer et al., "Yield potential and response of Roundup Ready soybean varieties to raptor or pursuit herbicides," Kansas State University, 1998.

Klee et al., "Cloning of an *Arabidopsis thaliana* gene encoding 5-enolpyruvylshikimate-3-phosphate synthase: sequence analysis and manipulation to obtain glyphosate-tolerant plants," *Mol. Gen Genet*, 210(3):437-442, 1987.

Lloyd et al., "Targeted mutagenesis using zinc-finger nucleases in *Arabidopsis*," *PNAS*, 102(6):2232-2237, 2005.

Monsanto Company, "Application for authorization to place on the market MONS 89788 soybean in the European Union, according to regulation (EC) No. 1829/2003 on genetically modified food and feed—Part II—Summary," Summary of the Dossier EFSA GMO NL 2006-36, pp. 1-31, 2006.

Office Action regarding U.S. Appl. No. 11/441,915, dated Oct. 20, 2008.

Office Action regarding U.S. Appl. No. 11/441,918, dated Jun. 16, 2008.

Padgette et al., "Development, identification, and characterization of a glyphosate-tolerant soybean line," *Crop Sci.*, 35:1451-1461, 1995.

Padgette et al., "Site-directed mutagenesis of a conserved region of the 5-enolpyruvylshikimate-3-phosphate synthase active site," *J. Biological Chemistry*, 266(33):22364-22369, 1991.

PCT International Search Report for PCT/US2006/020323, Jan. 2, 2007.

Ramsdale et al., "Glyphosate tank-mixed with insecticides or fungicides," *North Central Weed Science Society*, 59:280-283, 2002.

Response to Office Action regarding U.S. Appl. No. 11/441,918, dated Sep. 14, 2008.

Richins et al., "Sequence of figwort mosaic virus DNA (caulimovirus group)," *Nucleic Acids Res.*, 15(20):8451-466, 1987.

Rott et al., "Detection and quantification of roundup ready soy in foods by conventional and real-time polymerase chain reaction," *Journal of Agricultural and Food Chemistry*, 52(16):5223-5232, 2004.

Sanogo et al., "Effects of herbicides on *Fusarium solani* f. sp. glycines and development of sudden death syndrome in glyphosate-tolerant soybean," *Amer. Phytopathological Society*, 90(1):57-66, 2000.

Smith et al., "A combinatorial approach to create artificial homing endonucleases cleaving chosen sequences," *Nucleic Acids Research*, 34(22):e149, 2006.

Song et al., "A new integrated genetic linkage map of the soybean," *Theor. Appl. Genetics*, 109:122-128, 2004.

Terry et al., "Event-specific detection of roundup ready soya using two different real time PCR detection chemistries," *Eur. Food Res. Technol.*, 213:425-431, 2001.

Windels et al., "Characterisation of the roundup ready soybean insert," *Eur. Food Res. Technol.*, 213:107-112, 2001.

Windels et al., "Development of a line specific GMO detection method: a case study," *Me. Fac. Ladbouww. Univ. Gent.*, 65(5b):459-462, 1999.

Wright et al., "High-frequency homologous recombination in plants mediated by zinc-finger nucleases," *The Plant Journal*, 44:693-705, 2005.

Zhou et al., "A Simple Method for Identifying Plant/T-DNA Junction Sequences Resulting from *Agrobacterium*-mediated DNA Transformation," *Plant Molecular Biology Reporter*, 15:246-254, 1997.

New England BioLabs Inc. 1998/99 Catalog, (NEB Catalog), pp. 121 and 284, undated.

Final Office Action regarding U.S. Appl. No. 11/801,114, dated Aug. 26, 2009.

Zambryski et al., "Tumor Induction by *Agrobacterium tumefaciens*: Analysis of the Boundaries of T-DNA," *J. Mol. Appl. Genet.* 1:361-370, 1982.

\* cited by examiner

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: chimeric molecule of soybean genome and
      transgene

<400> SEQUENCE: 1
tatcaagctc caaacactga                                              20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: chimeric molecule of soybean genomic sequence
      and transgene

<400> SEQUENCE: 2
taataacgct cagactctag                                              20

<210> SEQ ID NO 3
<211> LENGTH: 1222
<212> TYPE: DNA
<213> ORGANISM: Artificial Sequence
<220> FEATURE:
<221> NAME/KEY: misc_feature
<222> LOCATION: (1)..(1222)
<223> OTHER INFORMATION: chimeric molecule of soybean genomic DNA and
      transgene insert

<400> SEQUENCE: 3
cctgtacttc ccaaaacttc gcttccctga cccatcatat ccaggactgg acgattggct      60
tgattgatac cagatgggtg agtcgagtcc acctcggtag cggcatttat ggcaacgatt     120
gcagccacgt tgacctccat catttttttct catgctcatc atggcctcca tcatggtggt    180
catttggtct ttcatggcct ccatgtcggc cttcatctgc tcttgaactt catctatctc     240
actcatgatt ctagccttgg cacgtgtttg gtaagggtac cgtaaagcgc gttcgttctt     300
ttttattact atgattacat tttgacgatg atgatgattg taggaaagaa tgaaatgagt     360
aatgaaacaa ctaaataaac gtgaatgcat gacaatgata agttgctgaa gtattataaa     420
tttacatagg acattcagtg gaacgtaggg tcgaatcaaa tcctatttca ttaaaaacaa     480
tattgttcat cttgacagag ccaaagcata actagaaata caacatggac acatcagcga     540
ttcctaatta tgtgggtcat tagttcgacc atgtgttggc agtaacttga aagactatga     600
acttcatcgg gagcagagta tgtgtcagtc accgccttgg ctctggctaa caaccttggg     660
atctcttggc tctcatttag agtaagagca aatttgtcca tccatttcat ggcttcttta     720
tgcaataact ctatcacccc ttctcttgct tccctttcaa cctgcaaggt cgacactttt     780
gcctgttcgt cttctagcct tcgcccatga ctagcagcta ggttcacctt ctcttcatat     840
tggtcaatga ttatcaacat attttctttt gttttgctca actgttctct caaacttctc     900
ttcgatctct gacaactctt taacttatcc tctaacatca ggttttccat acttgatttg     960
tccctcttgg cttttctaag tttgagctcg ttactgctgc cccacaaagc ccctcgaaac    1020

```
ttgttcctgc tccactcttc cttttgggct ttttgtttc ccgctctagc gcttcaatcg    1080
tggttatcaa gctccaaaca ctgatagttt aaactgaagg cgggaaacga caatctgatc    1140
cccatcaagc tctagctaga gcggccgcgt tatcaagctt ctgcaggtcc tgctcgagtg    1200
gaagctaatt ctcagtccaa ag                                              1222

<210> SEQ ID NO 4
<211> LENGTH: 675
<212> TYPE: DNA
<213> ORGANISM: Artificial Sequence
<220> FEATURE:
<221> NAME/KEY: misc_feature
<222> LOCATION: (1)..(675)
<223> OTHER INFORMATION: chimeric DNA molecule of soybean genomic DNA
      and transgene insert

<400> SEQUENCE: 4
gccaattgat tgacaacatg catcaatcga cctgcagcca ctcgaagcgg ccgcatcgat      60
cgtgaagttt ctcatctaag cccccatttg gacgtgaatg tagacacgtc gaaataaaga    120
tttccgaatt agaataattt gtttattgct ttcgcctata aatacgacgg atcgtaattt    180
gtcgttttat caaaatgtac tttcattta taataacgct cagactctag tgactaccac    240
cttcactctc ctcaagcatt tcagcctctt ccccgctcag actccttagc tttgggagcc    300
aaattatccc ttacgttctc gacttcaacc atatgtgata gctgcctatg ataccatggc    360
tacttcccct tagttcttta tctttccttt ccgctttatt ccatgcctta ccgatcctct    420
gaagtgtctt tgcattagct tcattgaaac ctcacgcgat gaaaggtgtg atggtctcct    480
ccgatggcgc acttctcata gggtaaccta attgtcttac gaccaacata ggattataat    540
taatacaacc cctcgtccct ataaaaggga catttggaaa tccttcacat aagcataaca    600
ctcctacccc tctttctttc cactgtggga accaactaat ggacgctcct atcatgcctg    660
ccaagagttc ttccc                                                      675

<210> SEQ ID NO 5
<211> LENGTH: 21
<212> TYPE: DNA
<213> ORGANISM: Glycine max

<400> SEQUENCE: 5
cctgtacttc ccaaaacttc g                                               21

<210> SEQ ID NO 6
<211> LENGTH: 22
<212> TYPE: DNA
<213> ORGANISM: Figwort mosaic virus

<400> SEQUENCE: 6
ctttccactg agaattagct cc                                              22

<210> SEQ ID NO 7
<211> LENGTH: 24
<212> TYPE: DNA
<213> ORGANISM: Petunia hybrida

<400> SEQUENCE: 7
gccaattgat tgacaacatg catc                                            24

<210> SEQ ID NO 8
<211> LENGTH: 20
<212> TYPE: DNA
```

-continued

<213> ORGANISM: Glycine max

<400> SEQUENCE: 8
gggaagaact cttggcaggc         20

<210> SEQ ID NO 9
<211> LENGTH: 6466
<212> TYPE: DNA
<213> ORGANISM: Artificial Sequence
<220> FEATURE:
<221> NAME/KEY: misc_feature
<222> LOCATION: (1)..(6466)
<223> OTHER INFORMATION: Chimeric DNA molecule of soybean genomic DNA
      and transgene insert

<400> SEQUENCE: 9

```
tgggggctgc ctgtacttcc caaaacttcg cttccctgac ccatcatatc caggactgga     60
cgattggctt gattgatacc agatgggtga gtcgagtcca cctcggtagc ggcatttatg    120
gcaacgattg cagccacgtt gacctccatc attttttctc atgctcatca tggcctccat    180
catggtggtc atttggtctt tcatggcctc catgtcggcc ttcatctgct cttgaacttc    240
atctatctca ctcatgattc tagccttggc acgtgtttgg taagggtacc gtaaagcgcg    300
ttcgttcttt tttattacta tgattacatt ttgacgatga tgatgattgt aggaaagaat    360
gaaatgagta atgaaacaac taaataaacg tgaatgcatg acaatgataa gttgctgaag    420
tattataaat ttacatagga cattcagtgg aacgtagggt cgaatcaaat cctatttcat    480
taaaaacaat attgttcatc ttgacagagc caaagcataa ctagaaatac aacatggaca    540
catcagcgat tcctaattat gtgggtcatt agttcgacca tgtgttggca gtaacttgaa    600
agactatgaa cttcatcggg agcagagtat gtgtcagtca ccgccttggc tctggctaac    660
aaccttggga tctcttggct ctcatttaga gtaagagcaa atttgtccat ccatttcatg    720
gcttctttat gcaataactc tatcacccct tctcttgctt cccttcaac ctgcaaggtc    780 gacacttttg cctgttcgtc ttctagcctt cgcccatgac tagcagctag gttcaccttc    840
tcttcatatt ggtcaatgat tatcaacata ttttcttttg ttttgctcaa ctgttctctc    900
aaacttctct tcgatctctg acaactcttt aacttatcct ctaacatcag gttttccata    960
cttgatttgt ccctcttggc ttttctaagt ttgagctcgt tactgctgcc ccacaaagcc   1020
cctcgaaact tgttcctgct ccactcttcc ttttgggctt ttttgtttcc cgctctagcg   1080
cttcaatcgt ggttatcaag ctccaaacac tgatagttta aactgaaggc gggaaacgac   1140
aatctgatcc ccatcaagct ctagctagag cggccgcgtt atcaagcttc tgcaggtcct   1200
gctcgagtgg aagctaattc tcagtccaaa gcctcaacaa ggtcagggta cagagtctcc   1260
aaaccattag ccaaaagcta caggagatca atgaagaatc ttcaatcaaa gtaaactact   1320
gttccagcac atgcatcatg gtcagtaagt ttcagaaaaa gacatccacc gaagacttaa   1380
agttagtggg catctttgaa agtaatcttg tcaacatcga gcagctggct tgtggggacc   1440
agacaaaaaa ggaatggtgc agaattgtta ggcgcaccta ccaaaagcat ctttgccttt   1500
attgcaaaga taaagcagat tcctctagta caagtgggga acaaaataac gtggaaaaga   1560
gctgtcctga cagcccactc actaatgcgt atgacgaacg cagtgacgac cacaaaagaa   1620
ttagcttgag ctcaggattt agcagcattc cagattgggt tcaatcaaca aggtacgagc   1680
catatcactt tattcaaatt ggtatcgcca aaaccaagaa ggaactccca tcctcaaagg   1740
tttgtaagga agaattcgat atcaagcttg atatcggaag tttctctctt gagggaggtt   1800
gctcgtggaa tgggacacat atggttgtta taataaacca tttccattgt catgagattt   1860
```

```
tgaggttaat atatacttta cttgttcatt attttatttg gtgtttgaat aaatgatata    1920
aatggctctt gataatctgc attcattgag atatcaaata tttactctag agaagagtgt    1980
catatagatt gatggtccac aatcaatgaa attttggga gacgaacatg tataaccatt     2040
tgcttgaata accttaatta aaaggtgtga ttaaatgatg tttgtaacat gtagtactaa    2100
acattcataa aacacaacca acccaagagg tattgagtat tcacggctaa acaggggcat    2160
aatggtaatt taaagaatga tattatttta tgttaaaccc taacattggt ttcggattca    2220
acgctataaa taaaaccact ctcgttgctg attccattta tcgttcttat tgaccctagc    2280
cgctacacac ttttctgcga tatctctgag gtaagcgtta acgtacccctt agatcgttct   2340 ttttcttttt cgtctgctga tcgttgctca tattatttcg atgattgttg gattcgatgc    2400
tctttgttga ttgatcgttc tgaaaattct gatctgttgt ttagatttta tcgattgtta    2460
atatcaacgt ttcactgctt ctaaacgata atttattcat gaaactattt tcccattctg    2520
atcgatcttg ttttgagatt ttaatttgtt cgattgattg ttggttggtg gatctatata    2580
cgagtgaact tgttgatttg cgtatttaag atgtatgtcg atttgaattg tgattgggta    2640
attctggagt agcataacaa atccagtgtt cccttttct aagggtaatt ctcggattgt     2700
ttgctttata tctcttgaaa ttgccgattt gattgaattt agctcgctta gctcagatga    2760
tagagcacca caattttgt ggtagaaatc ggtttgactc cgatagcggc ttttactat     2820 gattgttttg tgttaaagat gattttcata atggttatat atgtctactg tttttattga    2880
ttcaatattt gattgttctt tttttgcag atttgttgac cagagatcta ccatggcgca    2940
agttagcaga atctgcaatg gtgtgcagaa cccatctctt atctccaatc tctcgaaatc    3000
cagtcaacgc aaatctccct tatcggtttc tctgaagacg cagcagcatc cacgagctta    3060
tccgatttcg tcgtcgtggg gattgaagaa gagtgggatg acgttaattg gctctgagct    3120
tcgtcctctt aaggtcatgt cttctgtttc cacggcgtgc atgcttcacg gtgcaagcag    3180
ccgtccagca actgctcgta agtcctctgg tctttctgga accgtccgta ttccaggtga    3240
caagtctatc tcccacaggt ccttcatgtt tggaggtctc gctagcggtg aaactcgtat    3300
caccggtctt ttggaaggtg aagatgttat caacactggt aaggctatgc aagctatggg    3360
tgccagaatc cgtaaggaag gtgatacttg gatcattgat ggtgttggta acggtggact    3420
ccttgctcct gaggctcctc tcgatttcgg taacgctgca actggttgcc gtttgactat    3480
gggtcttgtt ggtgtttacg atttcgatag cactttcatt ggtgacgctt ctctcactaa    3540
gcgtccaatg ggtcgtgtgt tgaacccact tcgcgaaatg ggtgtgcagg tgaagtctga    3600
agacggtgat cgtcttccag ttaccttgcg tggaccaaag actccaacgc caatcaccta    3660
cagggtacct atggcttccg ctcaagtgaa gtccgctgtt ctgcttgctg gtctcaacac    3720
cccaggtatc accactgtta tcgagccaat catgactcgt gaccacactg aaaagatgct    3780
tcaaggtttt ggtgctaacc ttaccgttga gactgatgct gacggtgtgc gtaccatccg    3840
tcttgaaggt cgtggtaagc tcaccggtca agtgattgat gttccaggtg atccatcctc    3900
tactgctttc ccattggttg ctgccttgct tgttccaggt tccgacgtca ccatccttaa    3960
cgttttgatg aacccaaccc gtactggtct catcttgact ctgcaggaaa tgggtgccga    4020
catcgaagtg atcaacccac gtcttgctgg tgagaaagac gtggctgact tgcgtgttcg    4080
ttcttctact ttgaagggtg ttactgttcc agaagaccgt gctccttcta tgatcgacga    4140
gtatccaatt ctcgctgttg cagctgcatt cgctgaaggt gctaccgtta tgaacggttt    4200
ggaagaactc cgtgttaagg aaagcgaccg tctttctgct gtcgcaaacg gtctcaagct    4260
```

```
caacggtgtt gattgcgatg aaggtgagac ttctctcgtc gtgcgtggtc gtcctgacgg    4320
taagggtctc ggtaacgctt ctggagcagc tgtcgctacc cacctcgatc accgtatcgc    4380
tatgagcttc ctcgttatgg gtctcgtttc tgaaaaccct gttactgttg atgatgctac    4440
tatgatcgct actagcttcc cagagttcat ggatttgatg gctggtcttg gagctaagat    4500
cgaactctcc gacactaagg ctgcttgatg agctcaagaa ttcgagctcg gtaccggatc    4560
ctctagctag agctttcgtt cgtatcatcg gtttcgacaa cgttcgtcaa gttcaatgca    4620
tcagtttcat tgcgcacaca ccagaatcct actgagtttg agtattatgg cattgggaaa    4680 actgttttc ttgtaccatt tgttgtgctt gtaatttact gtgttttta ttcggttttc       4740 gctatcgaac tgtgaaatgg aaatggatgg agaagagtta atgaatgata tggtcctttt    4800
gttcattctc aaattaatat tatttgtttt ttctcttatt tgttgtgtgt tgaatttgaa    4860
attataagag atatgcaaac attttgtttt gagtaaaaat gtgtcaaatc gtggcctcta    4920
atgaccgaag ttaatatgag gagtaaaaca cttgtagttg taccattatg cttattcact    4980
aggcaacaaa tatattttca gacctagaaa agctgcaaat gttactgaat acaagtatgt    5040
cctcttgtgt tttagacatt tatgaacttt cctttatgta attttccaga atccttgtca    5100
gattctaatc attgctttat aattatagtt atactcatgg atttgtagtt gagtatgaaa    5160 atattttta atgcatttta tgacttgcca attgattgac aacatgcatc aatcgacctg     5220
cagccactcg aagcggccgc atcgatcgtg aagtttctca tctaagcccc catttggacg    5280
tgaatgtaga cacgtcgaaa taagatttc cgaattagaa taatttgttt attgctttcg     5340
cctataaata cgacggatcg taatttgtcg ttttatcaaa atgtactttc atttttataat     5400 aacgctcaga ctctagtgac taccaccttc actctcctca agcatttcag cctcttcccc    5460
gctcagactc cttagctttg ggagccaaat tatcccttac gttctcgact tcaaccatat    5520
gtgatagctg cctatgatac catggctact tccccttagt tctttatctt tccttttccgc    5580 tttattccat gccttaccga tcctctgaag tgtctttgca ttagcttcat tgaaacctca    5640
cgcgatgaaa ggtgtgatgg tctcctccga tggcgcactt tcatagggt aacctaattg     5700 tcttacgacc aacataggat tataattaat acaaccctc gtccctataa aagggacatt      5760
tggaaatcct tcacataagc ataacactcc taccctctt tctttccact gtgggaacca      5820
actaatggac gctcctatca tgcctgccaa gagttcttcc caatttgcct cgtcctttcc    5880
tgagcacatg cgatgacctt gtatggggta gacagatcta ctttcatgat tgaagacgtg    5940
ggataccaac cacacataaa gagcaggcgc acaacagaaa atcctcgtag tgctcttctt    6000
gcatcttaag tcaaatgtat catacactta tgctaaaaca acaatgatcg gctttccctt    6060
gctatggtga taagcaagaa aagcatcgat tgctactaga tccaccaact cgtctacatt    6120
cgaaaatagt actatcccaa acactagcag tgctaatacg tcgatgaatg atgcccactc    6180
tccttggctg gccagagttt ccgccttctc ctccaatcac ttccttggta ttcccctac     6240 cctattccta ctttgcttca ctcagtctaa ttctcatttc gagatcttga caactcctgc    6300
tattctcgcc atagaaggat agtacccaga aaaaggtat ggcttccttc ctcctatcgg     6360
gcatcctaag atcccttcga actcctctat ggttggtgct aactgaaagt ccccaaaagt    6420
gaagcatctg agtgattggt catagtattg ggtgagagat gcgatg                   6466
```

<210> SEQ ID NO 10  
<211> LENGTH: 22  
<212> TYPE: DNA  
<213> ORGANISM: Artificial Sequence

```
<220> FEATURE:
<221> NAME/KEY: misc_feature
<222> LOCATION: (1)..(22)
<223> OTHER INFORMATION: synthetic primer molecule

<400> SEQUENCE: 10 cctttttgggc tttttttgttt cc                                              22

<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthetic primer molecule

<400> SEQUENCE: 11
cgtttcccgc cttcagttta                                                   20

<210> SEQ ID NO 12
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthetic primer molecule

<400> SEQUENCE: 12
tgtgtggtgt gacccattgg                                                   20

<210> SEQ ID NO 13
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: synthetic primer molecule

<400> SEQUENCE: 13
cctcaattgg gagatactgc actta                                             25

<210> SEQ ID NO 14
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: synthetic primer molecule

<400> SEQUENCE: 14
gtagtcacta gggtcagtaa agaatgtga                                         29

<210> SEQ ID NO 15
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: synthetic primer molecule

<400> SEQUENCE: 15
ttatcaagct ccaaacac                                                     18
```

```
<210> SEQ ID NO 16
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: synthetic primer molecule

<400> SEQUENCE: 16
tgagctcaaa gatatcaaca tg                                              22

<210> SEQ ID NO 17
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: synthetic primer moleucle

<400> SEQUENCE: 17
agttaaatca tagttaataa tc                                              22

<210> SEQ ID NO 18
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthetic primer molecule

<400> SEQUENCE: 18
tcccgctcta gcgcttcaat                                                 20

<210> SEQ ID NO 19
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: synthetic primer molecule

<400> SEQUENCE: 19
tcgagcagga cctgcagaa                                                  19

<210> SEQ ID NO 20
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: synthetic primer molecule

<400> SEQUENCE: 20
ctgaaggcgg gaaacgacaa tctg                                            24

<210> SEQ ID NO 21
<211> LENGTH: 1103
<212> TYPE: DNA
<213> ORGANISM: Glycine max

<400> SEQUENCE: 21
tgggggctgc ctgtacttcc caaaacttcg cttccctgac ccatcatatc caggactgga     60
cgattggctt gattgatacc agatgggtga gtcgagtcca cctcggtagc ggcatttatg    120
```

-continued

```
gcaacgattg cagccacgtt gacctccatc atttttctc atgctcatca tggcctccat      180
catggtggtc atttggtctt tcatggcctc catgtcggcc ttcatctgct cttgaacttc      240
atctatctca ctcatgattc tagccttggc acgtgtttgg taagggtacc gtaaagcgcg      300
ttcgttcttt tttattacta tgattacatt ttgacgatga tgatgattgt aggaaagaat      360
gaaatgagta atgaaacaac taaataaacg tgaatgcatg acaatgataa gttgctgaag      420
tattataaat ttacatagga cattcagtgg aacgtagggt cgaatcaaat cctatttcat      480
taaaaacaat attgttcatc ttgacagagc caaagcataa ctagaaatac aacatggaca      540
catcagcgat tcctaattat gtgggtcatt agttcgacca tgtgttggca gtaacttgaa      600
agactatgaa cttcatcggg agcagagtat gtgtcagtca ccgccttggc tctggctaac      660
aaccttggga tctcttggct ctcatttaga gtaagagcaa atttgtccat ccatttcatg      720
gcttctttat gcaataactc tatcacccct tctcttgctt cccttcaac ctgcaaggtc      780 gacacttttg cctgttcgtc ttctagcctt cgcccatgac tagcagctag gttcaccttc      840
tcttcatatt ggtcaatgat tatcaacata ttttcttttg ttttgctcaa ctgttctctc      900
aaacttctct tcgatctctg acaactcttt aacttatcct ctaacatcag gttttccata      960
cttgatttgt ccctcttggc ttttctaagt ttgagctcgt tactgctgcc ccacaaagcc     1020
cctcgaaact tgttcctgct ccactcttcc ttttgggctt ttttgtttcc cgctctagcg     1080
cttcaatcgt ggttatcaag ctc                                             1103
```

<210> SEQ ID NO 22
<211> LENGTH: 1060
<212> TYPE: DNA
<213> ORGANISM: Glycine max

<400> SEQUENCE: 22

```
cagactctag tgactaccac cttcactctc ctcaagcatt tcagcctctt ccccgctcag       60
actccttagc tttgggagcc aaattatccc ttacgttctc gacttcaacc atatgtgata      120
gctgcctatg ataccatggc tacttcccct tagttcttta tctttccttt ccgctttatt      180
ccatgcctta ccgatcctct gaagtgtctt tgcattagct tcattgaaac ctcacgcgat      240
gaaaggtgtg atggtctcct ccgatggcgc acttctcata gggtaaccta attgtcttac      300
gaccaacata ggattataat taatacaacc cctcgtccct ataaaaggga catttggaaa      360
tccttcacat aagcataaca ctcctacccc tcttttcttc cactgtggga accaactaat      420
ggacgctcct atcatgcctg ccaagagttc ttcccaattt gcctcgtcct ttcctgagca      480
catgcgatga cttgtatgg ggtagacaga tctactttca tgattgaaga cgtgggatac      540
caaccacaca taaagagcag gcgcacaaca gaaaatcctc gtagtgctct tcttgcatct      600
taagtcaaat gtatcataca cttatgctaa acaacaatg atcgggcttt ccttgctatg      660
gtgataagca agaaaagcat cgattgctac tagatccacc aactcgtcta cattcgaaaa      720
tagtactatc ccaaacacta gcagtgctaa tacgtcgatg aatgatgccc actctccttg      780
gctggccaga gttccgcct tctcctccaa tcacttcctt ggtattcccc taccctatt      840 cctactttgc ttcactcagt ctaattctca tttcgagatc ttgacaactc ctgctattct      900
cgccatagaa ggatagtacc cagaaaaaag gtatggcttc cttcctccta cgggcatcc      960 taagatccct tcgaactcct ctatggttgg tgctaactga aagtccccaa aagtgaagca     1020
tctgagtgat tggtcatagt attgggtgag agatgcgatg                           1060
```

SOYBEAN EVENT MON89788 AND METHODS FOR DETECTION THEREOF

This application is a divisional of U.S. application Ser. No. 11/441,914, filed May 26, 2006, now U.S. Pat. No. 7,632,985 which application claims the benefit of U.S. Provisional Application No. 60/685,584, filed May 27, 2005, the entire disclosures of which are herein incorporated by reference.

BACKGROUND OF THE INVENTION

1. Field of the Invention

The present invention relates to a new and distinctive transgenic soybean transformation event, designated MON89788, a soybean cultivar derived therefrom, and plant parts, seed, and products thereof. The invention also relates to assays for detecting the presence of a DNA molecule specific to MON89788 in a plant part extract or seed extract.

2. Description of Related Art

Soybean (*Glycine max*) is an important crop in many areas of the world. The methods of biotechnology have been applied to soybean for improvement of the agronomic traits and the quality of the product. One such agronomic trait important in soybean production is herbicide tolerance, in particular, tolerance to glyphosate herbicide. A herbicide tolerant soybean event would be a useful trait for managing weeds.

N-phosphonomethylglycine, also known as glyphosate, is a well-known herbicide that has activity on a broad spectrum of plant species. Glyphosate is the active ingredient of Roundup® (Monsanto Co., St. Louis, Mo.), a safe herbicide having a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants.

Glyphosate tolerance can be achieved by the expression of EPSPS variants that have lower affinity for glyphosate and therefore retain their catalytic activity in the presence of glyphosate (U.S. Pat. Nos. 5,633,435; 5,094,945; 4,535,060, and 6,040,497). Enzymes that degrade glyphosate in plant tissues (U.S. Pat. No. 5,463,175) are also capable of conferring cellular tolerance to glyphosate. Such genes are used for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (U.S. Pat. No. 6,689,880), cotton (U.S. Pat. No. 6,740,488), soybean (WO 9200377) and canola (US Patent Appl. 20040018518). The transgenes for glyphosate tolerance and the transgenes for tolerance to other herbicides, e.g. the bar gene, (Toki el al., 1992; Thompson et al., 1987; phosphinothricin acetyltransferase (DeBlock et al., 1987), for tolerance to glufosinate herbicide) are also useful as selectable markers or scorable markers and can provide a useful phenotype for selection of plants linked with other agronomically useful traits.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., 1988). For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well known polynucleic acid detection method such as the polymerase chain reaction (PCR) or DNA hybridization using polynucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA ("flanking DNA") adjacent to the inserted transgene DNA is known. An event-specific PCR assay is discussed, for example, by Windels et al. (1999), who identified glyphosate tolerant soybean event 40-3-2 by PCR using a primer set spanning the junction between the insert transgene and flanking DNA, specifically one primer that included sequence from the insert and a second primer that included sequence from flanking DNA. Transgenic plant event specific DNA detection methods have also been to described in U.S. Pat. Nos. 6,893,826; 6,825,400; 6,740,488; 6,733,974 and 6,689,880; 6,900,014 and 6,818,807, herein incorporated by reference in their entirety.

This invention relates to the glyphosate tolerant soybean event MON89788 (also referred to as MON19788 or GM_A19788) and to the DNA molecules contained in these soybean plants that are useful in detection methods for the plant and progeny thereof and plant tissues derived from MON89788.

SUMMARY OF THE INVENTION

The present invention provides a soybean transgenic event designated MON89788 (also referred to as MON19788) and progeny thereof having representative seed deposited with American Type Culture Collection (ATCC) with accession No. PTA-6708. Another aspect of the invention is the plant cells or regenerable parts of the plant and seeds of the soybean event MON89788. The invention also includes plant parts of soybean event MON89788 that include, but are not limited to a cell, pollen, ovule, flowers, shoots, roots, leaves, and products derived from MON89788, for example soybean meal, flour and oil.

One aspect of the invention provides compositions and methods for detecting the presence of a DNA transgene/ genomic junction region from a soybean event MON89788 plant or seed or products derived from plant parts or seed. DNA molecules are provided that comprise at least one transgene/genomic junction DNA molecule selected from the group consisting of SEQ ID NO:1 and SEQ ID NO:2, and complements thereof, wherein the junction molecule spans the insertion site that comprises a heterologous DNA inserted into the genome of the soybean cell and the genomic DNA from the soybean cell flanking the insertion site soybean event MON89788. Such junction sequences may, in one aspect of the invention, be defined as comprising nucleotides 1093-1113 or 5396-5416 of SEQ ID NO:9, respectively. In other aspects of the invention, the junctions may be defined as including additional portions of the flanking genome and transgene, for example, and may be defined as comprising one or more sequence as given by nucleotides 1073-1113, 1043-1113, 1093-1133, 1093-1163, 1043-1163, 5376-5416, 5346-5416, 5396-5436, 5396-5416, 5396-5466, or 5346-5466 of SEQ ID NO:9. Such sequences and plants and seeds comprising these sequences therefore form one aspect of the invention.

A novel DNA molecule is provided that is a DNA transgene/genomic region SEQ ID NO:3 or the complement thereof, from soybean event MON89788. A soybean plant and seed comprising SEQ ID NO:3 in its genome is an aspect of this invention. SEQ ID NO:3 further comprises SEQ ID NO:1 in its entirety.

According to another aspect of the invention, a DNA molecule is provided that is a DNA transgene/genomic region SEQ ID NO:4, or the complement thereof, wherein this DNA molecule is novel in soybean event MON89788. A soybean plant and seed comprising SEQ ID NO:4 in its genome is an aspect of this invention. SEQ ID NO:4 further comprises SEQ ID NO:2 in its entirety.

According to another aspect of the invention, two nucleic acid molecules are provided for use in a DNA detection method, wherein the first nucleic acid molecule comprises at least 11 or more contiguous polynucleotides of any portion of the transgene region of the DNA molecule of SEQ ID NO:3 and the second nucleic acid is a molecule of similar length of any portion of a 5' flanking soybean genomic DNA region of SEQ ID NO:3, wherein these nucleic acid molecules when used together are useful as primers in a DNA amplification method that produces an amplicon. The amplicon produced using these primers in the DNA amplification method is diagnostic for soybean event MON89788 DNA. The amplicon produced by the described primers that is homologous or complementary to a portion of SEQ ID NO:3 comprising SEQ ID NO:1 is an aspect of the invention.

According to another aspect of the invention, two nucleic acid molecules are provided for use in a DNA detection method, wherein the first nucleic acid molecule comprises at least 11 or more contiguous polynucleotides of any portion of the transgene region of the DNA molecule of SEQ ID NO:4 and a second nucleic acid molecule of similar length of any portion of a 3' flanking soybean genomic DNA of SEQ ID NO:4, wherein these nucleic acid molecules when used together are useful as primers in a DNA amplification method that produces an amplicon. The amplicon produced using these primers in the DNA amplification method is diagnostic for soybean event MON89788 DNA. The amplicon produced by the described primers that is homologous or complementary to a portion of SEQ ID NO:4 comprising SEQ ID NO:2 is an aspect of the invention.

Any nucleic acid primer pair derived from SEQ ID NO:3 or SEQ ID NO:4, or SEQ ID NO:9 or the complements thereof, that when used in a DNA amplification reaction produces an amplicon diagnostic for soybean event MON89788-derived tissue, such as an amplicon that comprises SEQ ID NO:1 or SEQ ID NO:2 or any portion of SEQ ID NO:9 respectively, is another embodiment of the invention. In a particular embodiment, the primer pair may consist of primer A (SEQ ID NO:5) and primer D (SEQ ID NO:8).

Another aspect of the invention is a soybean plant, or seed, or product derived from a plant or seed comprising event MON89788, in which the genomic DNA when isolated from the soybean plant, or seed, or product produces an amplicon in a DNA amplification method that comprises SEQ ID NO:1 or SEQ ID NO:2.

Still another aspect of the invention is a soybean plant, or seed, or product derived from a plant or seed comprising MON89788, in which the genomic DNA when isolated from the soybean plant, or seed, or product produces an amplicon in a DNA amplification method, wherein DNA primer molecules SEQ ID NO:5 and SEQ ID NO:6 are used in the DNA amplification method.

Yet another aspect of the invention is a soybean plant, seed, product, or commodity derived from the plant or seed, comprising MON89788, in which the genomic DNA when isolated from the soybean plant, or seed, or product produces an amplicon in a DNA amplification method, wherein DNA primer molecules SEQ ID NO:7 and SEQ ID NO:8 are used in the DNA amplification method. The product or commodity may comprise, without limitation, a food or feed product comprising or derived from one or more of the following products of a soybean plant comprising event MON89788: lecithin, fatty acids, glycerol, sterol, edible oil, defatted soy flakes, soy meals including defatted and toasted soy meals, soy milk curd, tofu, soy flour, soy protein concentrate, isolated soy protein, hydrolyzed vegetable protein, textured soy protein, and soy protein fiber.

According to another aspect of the invention, a method of detecting the presence of DNA corresponding specifically to the soybean event MON89788 DNA in a sample is provided. Such method comprising: (a) contacting a sample comprising DNA with a DNA primer pair; (b) performing a nucleic acid amplification reaction, thereby producing the amplicon; and (c) detecting the amplicon, wherein said amplicon comprises SEQ ID NO:1 or SEQ ID NO:2. A kit comprising DNA primer molecules that when used in a DNA amplification method produces an amplicon comprising SEQ ID NO:1 or SEQ ID NO:2 is a further aspect of the invention.

According to another aspect of the invention, a method of detecting the presence of DNA corresponding specifically to the soybean event MON89788 DNA in a sample is provided. Such method comprising: (a) contacting a sample comprising DNA with a probe that hybridizes under stringent hybridization conditions with genomic DNA from soybean event MON89788 and does not hybridize under the stringent hybridization conditions with a control soybean plant DNA; (b) subjecting the sample and probe to stringent hybridization conditions; and (c) detecting hybridization of the probe to the soybean event MON89788 DNA, wherein said probe comprises SEQ ID NO:1 or SEQ ID NO:2. The sample may comprise a progeny seed, plant, or plant part comprising soybean event MON89788, or any of the following products derived from a plant comprising MON89788: lecithin, fatty acids, glycerol, sterol, edible oil, defatted soy flakes, soy meals including defatted and toasted soy meals, soy milk curd, tofu, soy flour, soy protein concentrate, isolated soy protein, hydrolyzed vegetable protein, textured soy protein, and soy protein fiber. A kit comprising a DNA probe comprising a DNA molecule that is homologous or complementary to SEQ ID NO:1 or SEQ ID NO:2 is an aspect of the invention. A kit comprising a DNA molecule comprising SEQ ID NO:18, SEQ ID NO:19, or SEQ ID NO:20, or their complements, is also an aspect of the invention.

According to another aspect of the invention, a method of producing a soybean plant that tolerates an application of glyphosate is provided that comprise the steps of: (a) sexually crossing a first parental glyphosate tolerant soybean plant comprising event MON89788, and a second parental soybean plant that lacks the glyphosate tolerance, thereby producing a plurality of progeny plants; and (b) selecting a progeny plant that tolerates application of glyphosate. Breeding methods may additionally comprise the steps of crossing the parental plant comprising soybean event MON89788 to a second parental soybean plant that is also tolerant to glyphosate and selecting for glyphosate tolerant progeny by molecular marker DNA genetically linked to the glyphosate tolerant phenotype found in each parent.

Another aspect of the invention is a method to control weeds in a field of soybean plants comprising MON89788, wherein said method comprises planting a field with soybean seed comprising event MON89788 said representative seed deposited as ATCC accession No. PTA-6708, allowing said seed to germinate and treating said plants with an effective dose of glyphosate to control weed growth in said field.

The foregoing and other aspects of the invention will become more apparent from the following detailed description and accompanying drawings.

DETAILED DESCRIPTION

Figure 1:
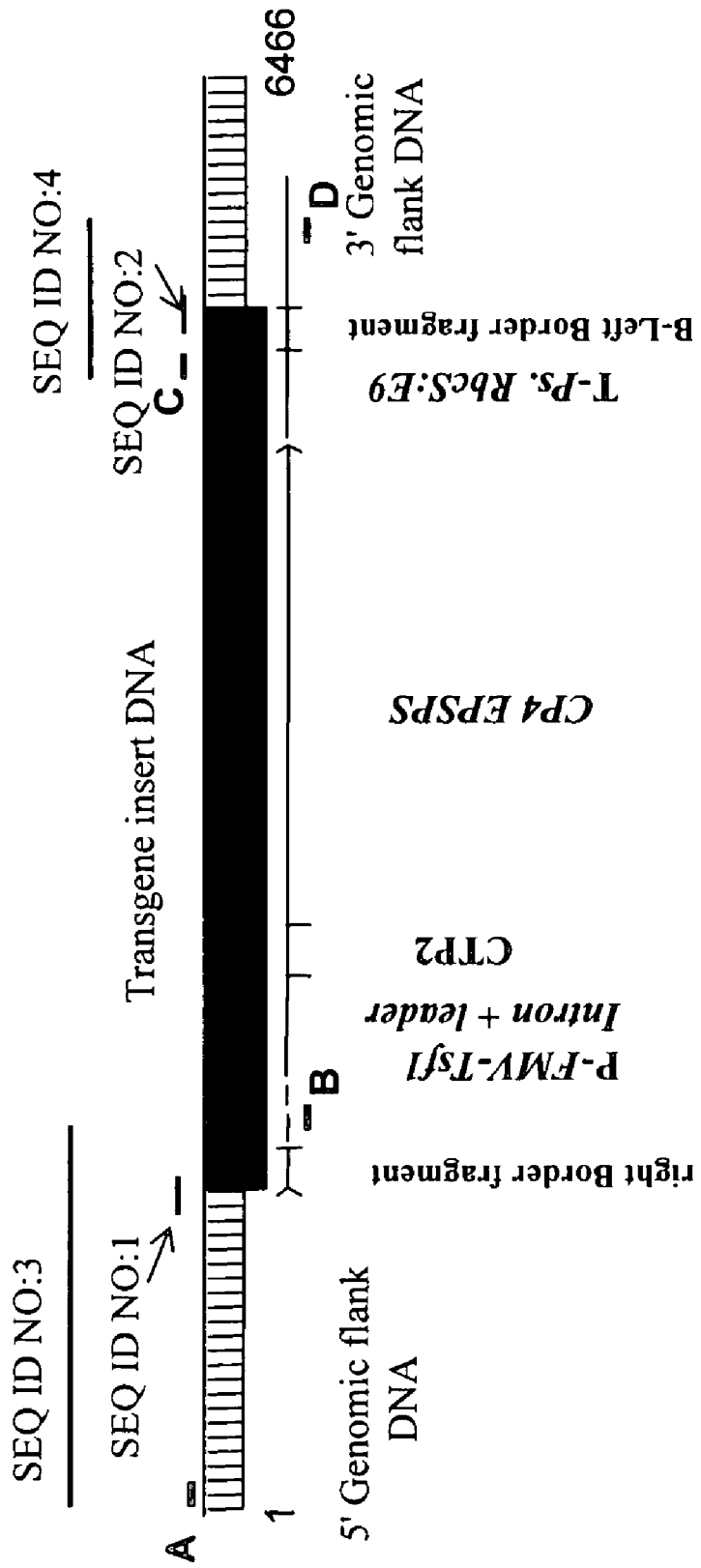
FIG. 1. Organization of the transgene insertion in the genome of a soybean plant comprising event MON89788.
Figure 2A:
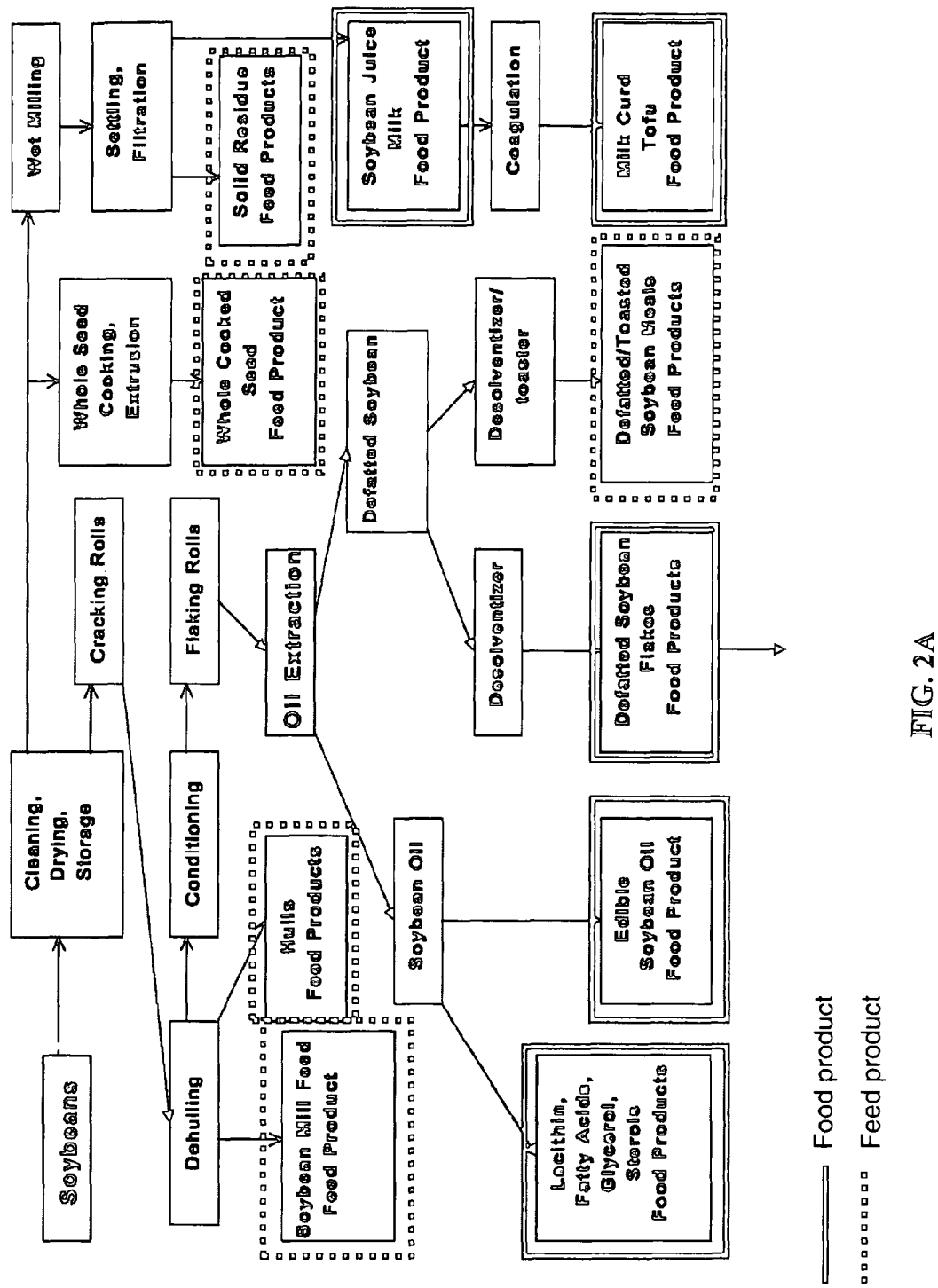
FIG. 2A-2B. Processing of commodity products from soybean.
Figure 2B:
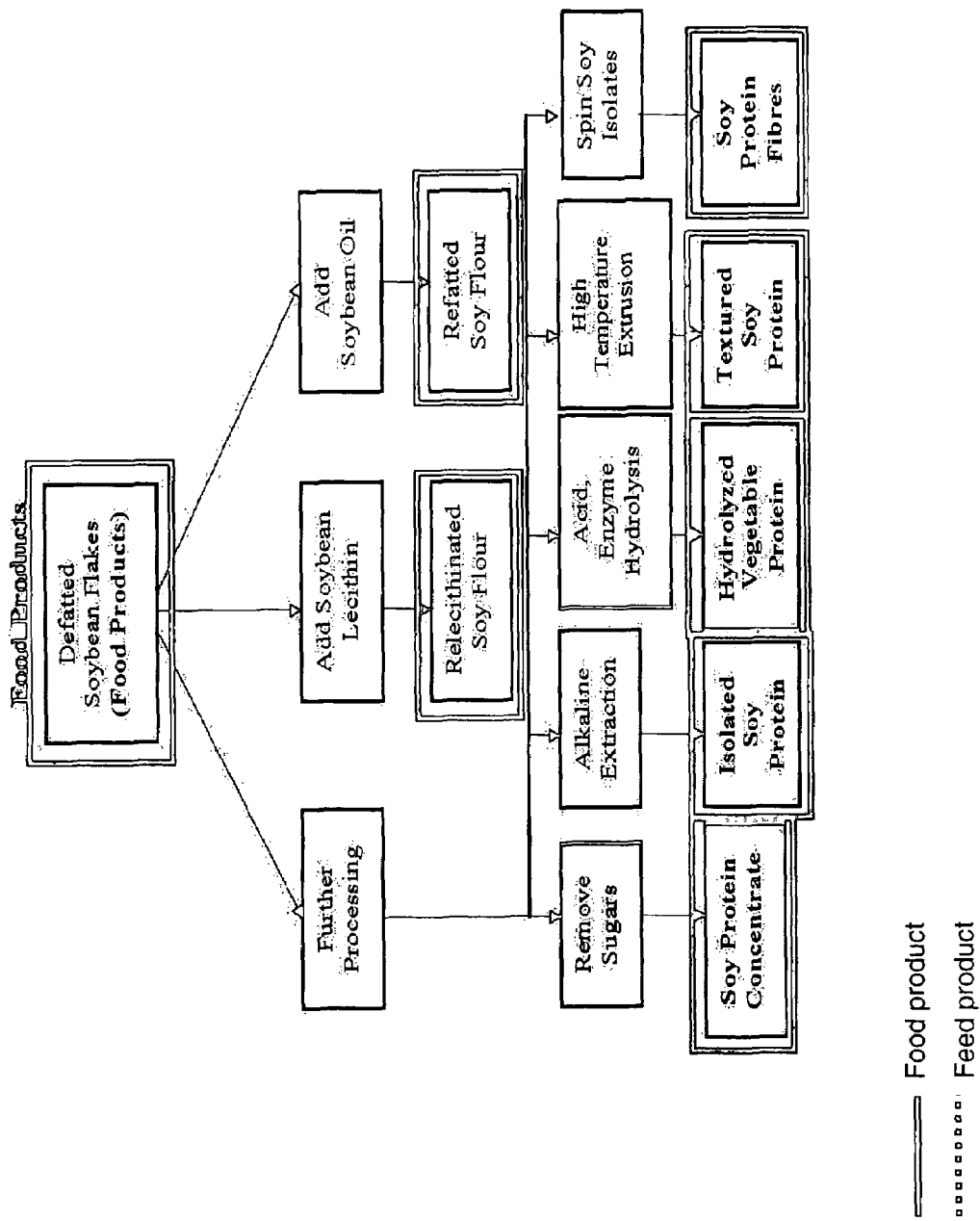

The present invention relates to a novel soybean transformation event designated MON89788 that provides glyphosate tolerance, and the plant parts and seed and products produced from plants, plant parts, seed, and products comprising the event. The invention provides DNA molecules that are novel in the genome of soybean cells comprising MON89788 and DNA molecules that can be used in various DNA detection methods to identify MON89788 DNA in a sample. The invention provides a method to control weeds in a field of plants containing MON89788 by treating the weeds in the field comprising plants comprising event MON89788 with a glyphosate herbicide.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al. (1991) and Lewin (1994). The nomenclature for DNA bases as set forth at 37 CFR §1.822 is used.

As used herein, the term "soybean" means *Glycine max* and includes all plant varieties that can be bred with soybean.

As used herein, the term "comprising" means "including but not limited to".

"Glyphosate" refers to N-phosphonomethylglycine and its salts, Glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation containing glyphosate. Examples of commercial formulations of glyphosate include, without restriction, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; ROUNDUP® WEATHERMAX (glyphosate potassium salt), those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Syngenta Crop Protection as TOUCHDOWN® herbicide, which contains glyphosate as its trimethylsulfonium salt. Treatment of a field comprising glyphosate tolerant soybean plants comprising event MON89788 with any of these glyphosate herbicide formulations will control weed growth in the field and not affect the growth or yield of the soybean plants comprising MON89788.

A transgenic "event" is produced by transformation of plant cells with heterologous DNA, for example, a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous transgene DNA and the flanking genomic DNA. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (for example, the original transformant and progeny resulting from the selling) and a parental line that does not contain the inserted DNA.

A glyphosate tolerant soybean plant can be bred by first sexually crossing a first parental soybean plant consisting of a soybean plant grown from a transgenic glyphosate tolerant soybean plant comprising MON89788 or an soybean plant that is a progeny of the cross of such a plant that expresses the glyphosate tolerant phenotype, and a second parental soybean plant that lacks the tolerance to glyphosate, thereby producing a plurality of first progeny plants; and then selecting a progeny plant that is tolerant to application of glyphosate herbicide. These steps can further include the back-crossing of the glyphosate tolerant progeny plant to the second parental soybean plant or a third parental soybean plant, then selecting progeny by application with glyphosate or by identification with molecular markers associated with the trait thereby producing an soybean plant that tolerates the application of glyphosate herbicide. Molecular markers may be used that comprise the junction DNA molecules identified at the 5' and 3' sites of insertion of the transgene in event MON89788.

It is also to be understood that two different transgenic plants can also be mated to produce offspring that contain two independently segregating, exogenous transgenes. Back-crossing to a parental plant and out-crossing with a non-transgenic plant as previously described is also contemplated, as is vegetative propagation. Descriptions of other breeding methods that are commonly used for different traits and crops can be found in one of several references, e.g., Fehr, (1987).

A "probe" is an isolated nucleic acid to which is attached a conventional detectable label or reporter molecule, for example, a radioactive isotope, a ligand, a chemiluminescent agent, or an enzyme. Such a probe is complementary to a strand of a target nucleic acid, in the case of the present invention, to a strand of genomic DNA from a soybean plant comprising event MON89788 whether from a soybean plant or seed or from a sample or extract of the plant or seed that includes DNA from the event. Probes according to the present invention include not only deoxyribonucleic or ribonucleic acids, but also polyamides and other probe materials that bind specifically to a target DNA sequence and can be used to detect the presence of that target DNA sequence.

"Primers" are isolated polynucleic acids that are annealed to a complementary target polynucleic acid strand by nucleic acid hybridization to form a hybrid between the primer and the target polynucleic acid strand, then extended along the target polynucleic acid strand by a polymerase, for example, a DNA polymerase. Primer pairs of the present invention refer to their use for amplification of a target polynucleic acid molecule, for example, by the polymerase chain reaction (PCR) or other conventional nucleic acid amplification methods.

Probes and primers are generally 11 polynucleotides or more in length, preferably 18 polynucleotides or more, more preferably 24 polynucleotides or 30 polynucleotides or more. Such probes and primers hybridize specifically to a target molecule under high stringency hybridization conditions. Preferably, probes and primers according to the present invention have complete sequence identity with the target molecule, although probes differing from the target sequence and that retain the ability to hybridize to target sequences under high stringency conditions may be designed by conventional methods.

Methods for preparing and using probes and primers are described, for example, in Sambrook et al. (1989); Ausubel et al. (1992); and Innis et al. (1990). PCR-primer pairs (a primer set) can be derived from a known sequence, for example, by using computer programs intended for that purpose such as Primer (Version 0.5, © 1991, Whitehead Institute for Biomedical Research, Cambridge, Mass.).

Primers and probes based on the flanking genomic DNA and insert sequences disclosed herein (SEQ ID NOs:1-4 and 9) can be used to confirm and, if necessary, to correct the disclosed sequences by conventional methods, for example, by isolating the corresponding DNA molecule from a deposit of seed comprising MON89788, and determining the nucleic acid sequence such molecules. Additional associated DNA molecules may be isolated from the genome of a cell comprising MON89788 that comprise the transgene insert and genomic flanking regions, and fragments of these molecules may be used as primers or probes.

The nucleic acid probes and primers of the present invention hybridize under stringent conditions to a target DNA sequence. Any conventional nucleic acid hybridization or amplification method can be used to identify the presence of DNA from the MON89788 event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure and are of sufficient length to maintain this structure under high stringency conditions. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NOs:1-4, and 9 complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NOs:1-4, and 9 complements thereof or fragments of either under high stringency conditions. In one aspect of the present invention, a preferred marker nucleic acid molecule of the present invention comprises the nucleic acid sequence as set forth in SEQ ID NO:1 or SEQ ID NO:2 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:1 or SEQ ID NO:2 or complements thereof or fragments of either. Molecular marker DNA molecules that comprise SEQ ID NO:1, or SEQ ID NO:2, or complements thereof or fragments of either may be used as markers in plant breeding methods to identify the progeny of genetic crosses similar to the methods described for simple sequence repeat DNA marker analysis, in Cregan et al. (1997); all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (for example, by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether the soybean plant resulting from a sexual cross contains transgenic event MON89788 or whether a soybean sample collected from a field comprises MON89788, or a soybean extract, such as a meal, flour or oil comprises MON89788. DNA extracted from a soybean plant tissue sample or extract may be subjected to a nucleic acid amplification method using a primer pair that includes a primer derived from the genomic region adjacent to the insertion site of inserted heterologous transgene DNA, and a second primer derived from the inserted heterologous transgene DNA to produce an amplicon that is diagnostic for the presence of the event DNA. The amplicon is of a length and has a sequence that is also diagnostic for the event. The amplicon may range in length from the combined length of the primer pairs plus one nucleotide base pair, or plus about fifty nucleotide base pairs, or plus about two hundred-fifty nucleotide base pairs, or plus about three hundred-fifty nucleotide base pairs or more.

Alternatively, a primer pair can be derived from flanking genomic sequence on both sides of the inserted DNA so as to produce an amplicon that includes the entire insert nucleotide sequence. A member of a primer pair derived from the plant genomic sequence may be located a distance from the inserted transgene DNA molecule, this distance can range from one nucleotide base pair up to about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification reaction methods known in the art, including the polymerase chain reaction (PCR). A variety of amplification methods are known in the art and are described, inter alia, in U.S. Pat. Nos. 4,683,195 and 4,683,202 and in Innis et al. (1990). PCR amplification methods have been developed to amplify up to 22 kb of genomic DNA and up to 42 kb of bacteriophage DNA (Cheng et al., 1994). These methods as well as other methods known in the art of DNA amplification may be used in the practice of the present invention. The sequence of the heterologous DNA insert or flanking sequence from soybean event MON89788 and can be verified, and corrected if necessary by amplifying such molecules from the event genome using primers derived from the sequences provided herein followed by standard DNA sequencing methods applied to the PCR amplicon or to isolated cloned transgene/genomic DNA.

The amplicon produced by these methods may be detected by a plurality of techniques. One such method is Genetic Bit Analysis (Nikiforov, et al., 1994) where an DNA oligonucleotide is designed which overlaps both the adjacent flanking genomic DNA sequence and the inserted DNA transgene sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking genomic sequence due to successful amplification, hybridization, and single base extension.

Another method is the Pyrosequencing technique as described by Winge (2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al. (1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking genomic/transgene insert sequence due to successful amplification and hybridization.

Molecular Beacons have been described for use in sequence detection as described in Tyangi et al. (1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Other described methods, such as, microfluidics (US Patent Pub. 2006068398, U.S. Pat. No. 6,544,734) provide methods and devices to separate and amplify DNA samples. Optical dyes used to detect and quantitate specific DNA molecules (WO/05017181). Nanotube devices (WO/06024023) that comprise an electronic sensor for the detection of DNA molecules or nanobeads that bind specific DNA molecules and can then be detected are useful for detecting DNA molecules of the present invention.

DNA detection kits can be developed using the compositions disclosed herein and the methods described or known in the art of DNA detection. The kits are useful for the identification of soybean event DNA in a sample and can be applied to methods for breeding soybean plants containing DNA. The kits may contain DNA primers or probes that are homologous or complementary to SEQ ID NOs:1-4 and 9 or DNA primers or probes homologous or complementary to DNA contained in the transgene genetic elements of DNA, these DNA sequences can be used in DNA amplification reactions or as probes in a DNA hybridization method. The structure of the DNA of the transgene genetic elements contained in the soybean genome and illustrated in FIG. 1 comprises a 5' genomic region of the soybean A3244 genome flanking the transgene insert, the insert comprising a portion of the right border region (RB) from *Agrobacterium tumefaciens*, the chimeric promoter FMV/Tsf1 and related linked elements (U.S. Pat. No. 6,660,911; also referred to as FMV/E1F1α) is operably connected to an *Arabidopsis* EPSPS chloroplast transit peptide coding sequence (herein referred to as CTP2 or TS-AtEPSPS CTP2, U.S. Pat. No. 5,633,435, operably connected to a glyphosate resistant EPSPS (herein referred to as CP4 EPSPS or aroA:CP4, isolated from *Agrobacterium tumefaciens* strain CP4 and coding sequence modified for enhanced expression in plant cells, U.S. Pat. No. 5,633,435), operably connected to the 3' termination, region from pea ribulose 1,5-bisphosphate carboxylase (herein referred to as E9 3' or T-Ps.RbcS:E9, Coruzzi et al., (1984), a portion of the left border (LB) region from *Agrobacterium tumefaciens*, and the 3' genomic region of the soybean A3244 genome flanking the transgene insert. DNA molecules useful as primers in DNA amplification methods can be derived from the sequences of the genetic elements of the transgene insert contained in soybean event MON89788. These primer molecules can be used as part of a primer set that also includes a DNA primer molecule derived from the genome of soybean flanking the transgene insert. Soybean event MON89788 was produced by transformation of soybean line A3244 (U.S. Pat. No. 5,659,114) by an *Agrobacterium* mediated method, for example, methods described in U.S. Pat. Nos. 6,384,301 and 7,002,058 (herein incorporated by reference in their entirety).

The inventors of the present invention have discovered that a soybean line comprising the MON89788 T-type genomic region (T-type is combination of a transgene and the associated haplotype region of a plant genome) in its genome has an improved yield relative to a line comprising the previous 40-3-2 T-type genomic region. This was demonstrated in replicated field trials including yield data collected from multiple locations in the United States (U.S. patent application 60/685,584).

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Production of Amplicon Diagnostic for MON89788 Genomic DNA

DNA from transgenic soybean event MON89788 is extracted from tissue comprising soybean seeds, vegetative tissue, or meal. The DNA is isolated from the tissue using Qiagen's DNeasy Plant Miniprep Kit according to the manufacturer's instructions (Qiagen Corp. Valencia, Calif.).

A PCR product is produced that comprises a portion of the genomic DNA flanking the 5' end of the T-DNA (transfer DNA comprising the transgene) insertion in the genome of a plant comprising MON89788. This DNA product comprises SEQ ID NO:3. The PCR may be performed using one primer designed to hybridize to the genomic DNA sequences flanking the 5' end of the transgene insert (DNA primer A, SEQ ID NO:5; see FIG. 1) paired with a second primer (DNA primer B, SEQ ID NO:6) located in the transgene promoter region (U.S. Pat. No. 6,660,911, SEQ ID NO:28, herein incorporated by reference and found within SEQ ID NO:9).

A PCR product is produced from the 3' end of the transgene insert that comprises a portion of the genomic DNA flanking the 3' end of the T-DNA insertion in the genome of a plant comprising MON89788 This DNA product comprises SEQ ID NO:4. PCR may be performed using one primer designed to hybridize to the genomic DNA sequences flanking the 3' end of the insert of each event (DNA primer D, SEQ ID NO:8) and paired with a second primer (DNA primer C, SEQ ID NO:7) located in the T-Ps.RbcS:E9 3' transcription termination sequence at the 3' end of the insert.

The PCR template includes ~50 ng of genomic DNA. As a negative control ~50 ng of genomic DNA from the non-transgenic soybean cultivar is utilized. Each PCR reaction contains 5 µl 10× Buffer for REDAccuTaq™ LA DNA Polymerase Mix (Sigma-Aldrich, St Louis, Mo.), 200 µM each dNTP (Sigma-Aldrich), 0.4 µM each primer, and 2.5 Units JumpStart™ REDTaq™ DNA Polymerase (Sigma-Aldrich) in a 50 µl total volume reaction. The PCR reactions are performed under the following cycling conditions: 1 cycle at 94° C. for 3 minutes (min); 32 or 35 cycles at 94° C. for 30 seconds (s), 58° C. for 30 s, 72° C. for 30 s or 1 min; 1 cycle at 72° C. for 10 min.

DNA event primer pairs are used to produce an amplicon diagnostic for MON89788 genomic DNA. These event primer pairs include, but are not limited to primers A and B (SEQ ID NO:5 and 6) and event primer pairs C and D (SEQ ID NO: 7 and 8), that are used in the described DNA amplification method. In addition to these primer pairs, any primer pair derived from SEQ ID NO:3 or SEQ ID NO:4, or the complements thereof, that when used in a DNA amplification reaction produces an amplicon that comprises SEQ ID NO:1 or SEQ ID NO:2 diagnostic for soybean MON89788 event-derived tissue, respectively, may be utilized. DNA amplification conditions illustrated in Table 1 and Table 2 can be used to produce a diagnostic amplicon for MON89788 using the appropriate event primer pairs. Any modification of these methods used to produce an amplicon diagnostic for MON89788 is within the ordinary skill of the art. An extract putatively containing DNA of a soybean plant or seed comprising MON89788, or a product derived from a plant comprising MON89788 that when tested in a DNA amplification method produces an amplicon diagnostic for soybean event MON89788 may be utilized as a template for amplification to determine whether MON89788 is present.

The amplicon is produced by the use of at least one primer sequence derived from SEQ ID NO:3 or SEQ ID NO:4 that when used in a PCR method produces a diagnostic amplicon for event MON89788. For example, the production of the MON89788 amplicons can be performed using a Stratagene Robocycler, MJ Engine, Perkin-Elmer 9700, or Eppendorf Mastercycler Gradient thermocycler as shown in Table 2, or by methods and apparatus known to those skilled in the art.

TABLE 1

PCR procedure and reaction mixture conditions for the identification of soybean MON89788 5' transgene insert/genomic junction region.

| Step | Reagent | Amount | Comments |
|------|---------|--------|----------|
| 1 | Nuclease-free water | add to final volume of 20 μl | — |
| 2 | 10X reaction buffer (with MgCl$_2$) | 2.0 μl | 1X final concentration of buffer, 1.5 mM final concentration of MgCl$_2$ |
| 3 | 10 mM solution of dATP, dCTP, dGTP, and dTTP | 0.4 μl | 200 μM final concentration of each dNTP |
| 4 | Event primer A (SEQ ID NO: 5 resuspended in 1X TE buffer or nuclease-free water to a concentration of 10 μM) | 0.2 μl | 0.1 μM final concentration |
| 5 | Event primer B (SEQ ID NO: 6 resuspended in 1X TE buffer or nuclease-free water to a concentration of 10 μM) | 0.2 μl | 0.1 μM final concentration |
| 6 | RNase, DNase free (500 μg/ml) | 0.1 μl | 50 ng/reaction |
| 7 | REDTaq DNA polymerase (1 unit/μl) | 1.0 μl (recommended to switch pipets prior to next step) | 1 unit/reaction |
| 8 | Extracted DNA (template): Samples to be analyzed: | | |
| | individual leaves | 10-200 ng of genomic DNA | |
| | pooled leaves (maximum of 10 leaves/pool) | 200 ng of genomic DNA | |
| | Negative control | 50 ng of non-transgenic soybean genomic DNA | |
| | Negative control | no template DNA (solution in which DNA was resuspended) | |
| | Positive control | 50 ng of soybean genomic DNA comprising MON89788 | |

Gently mix and, if needed (no hot top on thermocycler), add 1-2 drops of mineral oil on top of each reaction. Proceed with the PCR in a Stratagene Robocycler (Stratagene, La Jolla, Calif.), MJ Engine (MJR-Biorad, Hercules, Calif.), Perkin-Elmer 9700 (Perkin Elmer, Boston, Mass.), or Eppendorf Mastercycler Gradient (Eppendorf, Hamburg, Germany) thermocycler using the following cycling parameters (Table 2). The MJ Engine or Eppendorf Mastercycler Gradient thermocycler should be run in the calculated mode. Run the Perkin-Elmer 9700 thermocycler with the ramp speed set at maximum.

TABLE 2

Thermocycler conditions

| Cycle No. | Settings: Stratagene Robocycler |
|-----------|-------------------------------|
| 1 | 94° C. 3 minutes |
| 34 | 94° C. 1 minute |
| | 64° C. 1 minute |
| | 72° C. 1 minute and 30 seconds |
| 1 | 72° C. 10 minutes |

| Cycle No. | Settings: MJ Engine or Perkin-Elmer 9700 |
|-----------|------------------------------------------|
| 1 | 94° C. 3 minutes |
| 34 | 94° C. 30 seconds |
| | 64° C. 30 seconds |
| | 72° C. 1 minute |
| 1 | 72° C. 10 minutes |

TABLE 2-continued

Thermocycler conditions

| Cycle No. | Settings: Eppendorf Mastercycler Gradient |
|-----------|-------------------------------------------|
| 1 | 94° C. 3 minutes |
| 34 | 94° C. 15 seconds |
| | 64° C. 15 seconds |
| | 72° C. 1 minute |
| 1 | 72° C. 10 minutes |

Example 2

Sequence Determination of Transgene/Genomic Region and Southern Analysis

DNA sequencing of the PCR products provides for DNA that can be used to design additional DNA molecules as primers and probes for the identification of soybean plants or seed comprising MON89788. PCR products of the expected sizes representing the 5' and 3' transgene/genomic sequences were isolated by separation of the PCR products on a 2.0% agarose gel by electrophoresis. PCR products are isolated that include the 5' and 3' DNA regions that span the insert junction between the transgene insertion into the soybean genome. The 5' and 3' PCR products for MON89788 are purified by agarose gel electrophoresis followed by isolation from the agarose matrix using the QIAquick Gel Extraction Kit (catalog #28704, Qiagen Inc., Valencia, Calif.). The purified PCR products are then sequenced (e.g. ABI Prism™ 377, PE Biosystems, Foster City, Calif.) and analyzed (e.g. DNASTAR sequence analysis software, DNASTAR Inc., Madison, Wis.).

A DNA sequence was determined for the nucleotide base pair segment representing the transgene/genomic region of event MON89788 as illustrated in FIG. 1 and identified as SEQ ID NO:9. The genomic and transgene elements that are contained in SEQ ID NO:9 are described in Table 3. The 5' and 3' flanking regions are included in SEQ ID NO:9 and given in SEQ ID NOs:21 and 22.

PB57-VIC (SEQ ID NO:17). The primers and probes were used in the Taqman® method according to manufacturers instructions to provide a diagnostic amplicon for DNA comprising MON89788. Soybean tissues including processed products, for example meal, are useful sources of DNA for this method. Additional primers used to produce an amplicon from soymeal include SEQ ID NOs:18-20.

TABLE 3

Genome and genetic element annotation of the transgene/genomic DNA fragment (SEQ ID NO: 9) contained in the genome of soybean comprising MON89788.

| Genetic Element[1] | Location in Sequence[2] | Function (Reference) |
|---|---|---|
| Sequence flanking 5' end of the insert | 1-1103 | SOYBEAN GENOMIC DNA |
| 5'Junction region | 1093-1113 | DNA region spanning the transgene insertion |
| B[3]-Right Border | 1104-1145 | DNA region from *Agrobacterium tumefaciens* containing the right border sequence used for transfer of the T-DNA (Depicker et al., 1982) |
| Intervening Sequence | 1146-1215 | Sequences used in DNA cloning |
| P[4]-FMV/Tsf1 | 1216-2255 | Chimeric promoter consisting of enhancer sequences from the 35S promoter of the Figwort Mosaic virus (Richins et al., 1987) and the promoter from the Tsf1 gene of *Arabidopsis thaliana* (encoding elongation factor EF-1 alpha (Axelos, et al., 1989) |
| L[5]-Tsf1 | 2256-2301 | 5' nontranslated leader (exon 1) from the Tsf1 gene of *Arabidopsis thaliana* encoding elongation factor EF-1 alpha (Axelos et al., 1989) |
| I[6]-Tsf1 | 2302-2923 | Intron from the Tsf1 gene of *Arabidopsis thaliana* encoding elongation factor EF-1 alpha (Axelos et al., 1989) |
| Intervening Sequence | 2924-2932 | SEQUENCES USED IN DNA CLONING |
| TS[7]-CTP2 | 2933-3160 | Sequences encoding the chloroplast transit peptide from the ShkG gene of *Arabidopsis thaliana* encoding EPSPS (Klee et al., 1987) |
| CS[8]-cp4 epsps | 3161-4528 | Codon optimized coding sequence of the aroA gene from the *Agrobacterium* sp. strain CP4 encoding the CP4 EPSPS protein (Padgette et al., 1996; Barry et al., 1997) |
| Intervening Sequence | 4529-4570 | Sequences used in DNA cloning |
| T[9]-E9 | 4571-5213 | 3' nontranslated sequence from the RbcS2 gene of *Pisum sativum* encoding the Rubisco small subunit (Coruzzi et al., 1984) |
| Intervening Sequence | 5214-5256 | Sequences used in DNA cloning |
| B-Left Border | 5257-5406 | DNA region from *Agrobacterium tumefaciens* containing the left border sequence used for transfer of the T-DNA (Barker et al., 1983) |
| 3' junction region | 5396-5416 | DNA region spanning the transgene insertion |
| Sequence flanking 3' end of the insert | 5407-6466 | Soybean genomic DNA |

The junction sequences are relatively short polynucleotide molecules that are novel DNA sequences and are diagnostic for MON89788 DNA when detected in a polynucleic acid detection assay. The junction sequences in SEQ ID NO:1 and SEQ ID NO:2 represent 10 polynucleotides on each side of an insertion site of the transgene fragment and soybean genomic DNA in MON89788. Longer or shorter polynucleotide junction sequences can be selected from SEQ ID NO:3 or SEQ ID NO:4. The junction molecules (5' junction region SEQ ID NO:1, and 3' junction region SEQ ID NO:2) are useful as DNA probes or as DNA primer molecules in methods for DNA detection.

Primers and probes used in a Taqman® method (Roche Molecular Systems, Inc., Pleasanton, Calif.) for detection of an event specific DNA molecule were developed for event MON89788. The primer molecules are referred to as SQ2824 (SEQ ID NO:10), SQ2826 (SEQ ID NO:11), SQ1141 (SEQ ID NO:12), SQ1142 (SEQ ID NO:13), SQ5543 (SEQ ID NO:14) and the probe molecules are referred to as PB871-6FAM (SEQ ID NO:15), PB2191-VIC (SEQ ID NO:16), and Southern Blot Analysis Genomic DNA from a plant comprising MON89788 and control soybean genomic DNA (~15 μg of each) is digested with various restriction enzymes (140 U) in a total volume of 150 μl including 15 μl of the corresponding manufacturer's buffer (NEB, Beverly, Mass.). Restriction endonucleases, e.g., Bgl11, BamH1, Nco1, Hind111, and Bcl1, are used in the Southern analysis of MON89788. Endonuclease digests are performed at the appropriate temperature for at least 6 hours. After incubating, the DNA is precipitated with 3M sodium acetate and 2.5 volumes of ethanol. Subsequently, the DNA is washed with 70% ethanol, dried, and resuspended in 40 μl of TBE. Loading buffer (0.2x) is added to the samples and then subjected to electrophoresis on agarose gels (0.8%) for 16-18 hours at 30 volts. The gels are stained with ethidium-bromide, then treated with a depurination solution (0.125N HCL) for 10 minutes, with a denaturing solution (0.5M sodium hydroxide, 1.5M sodium chloride) for 30 minutes, and finally with a neutralizing solution (0.5M Trizma base, 1.5M sodium chloride) for 30 minutes. The DNA is transferred to Hybond-N membrane (Amersham Pharmacia Biotech, Buckinghamshire, England) using a Turboblotter (Schleicher and Schuell, Dassel, Germany) for 4-6 hours and then fixed to the membrane using a UV light.

Membranes are prehybridized with 20 mls of DIG Easy Hyb solution (Roche Molecular Biochemicals, Indianapolis, Ind.; cat. #1603558) for 2-4 hours at 45° C. Radioactive DNA probes ($^{32}$P dCTP) homologous or complementary to SEQ ID NO:1, or SEQ ID NO:2, or SEQ ID NO:3, or SEQ ID NO:4, or a portion thereof are made using a Radprime DNA Labeling kit (Invitrogen, Carlsbad, Calif.; cat. #18428-011). Unincorporated nucleotides are removed using SEPHADEX G-50 columns (Invitrogen). The prehybridization solution is replaced with 10 mls of pre-warmed DIG Easy Hyb solution containing the denatured probe to a final concentration of 1 million counts per ml. The blots are hybridized at 45° C. for 16-18 hours.

Blots are washed with a low stringency solution (5×SSC, 0.1×SDS) at 45° C. and then repeatedly washed with a higher stringency solution (0.1×SSC, 0.1% SDS) at 65° C. The blots are exposed to a phosphor screen (Amersham Biosciences, Piscataway, N.J.) for >2 hours and the exposure read using a Data Storm 860 machine (Amersham Biosciences). These methods and conditions exemplified may be modified by those skilled in the art of detecting DNA in a sample.

Example 3

Weed Control

Controlling the growth of weeds in a field of soybeans comprising MON89788. A field is planted with soybean seeds comprising MON89788, the seeds are allowed to germinate into plants and the field of plants is treated with a herbicide formulation containing glyphosate. An effective dose of a glyphosate formulation at treatment rates of from about 0.25 lb ae/A (pounds of glyphosate acid equivalent/acre) to 3 or more lb ae/A is applied to the field. Rates often applied range from about 0.75 lb ae/A to 1.5 lb ae/A at a frequency of one or more treatments during the growing season as necessary to control the growth of weeds in a field. Seeds from the plants comprising MON89788 are harvested from the treated plants.

A deposit of the Monsanto Technology LLC, soybean seed representative of event MON89788 disclosed above and recited in the claims has been made under the Budapest Treaty with the American Type Culture Collection (ATCC), 10801 University Boulevard, Manassas, Va. 20110. The ATCC accession number for the deposit comprising event MON89788 (also known as MON19788 or GM_A19788) is PTA-6708, deposited May 11, 2005. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

REFERENCES

The following references, to the extent that they provide exemplary procedural or other details supplementary to those set forth herein, are specifically incorporated herein by reference.

U.S. Pat. No. 4,535,060
U.S. Pat. No. 4,683,195
U.S. Pat. No. 4,683,202
U.S. Pat. No. 5,094,945
U.S. Pat. No. 5,463,175
U.S. Pat. No. 5,554,798
U.S. Pat. No. 5,633,435
U.S. Pat. No. 5,633,435
U.S. Pat. No. 5,659,114
U.S. Pat. No. 6,040,497
U.S. Pat. No. 6,384,301
U.S. Pat. No. 6,544,734
U.S. Pat. No. 6,660,911
U.S. Pat. No. 6,660,911
U.S. Pat. No. 6,689,880
U.S. Pat. No. 6,689,880
U.S. Pat. No. 6,733,974
U.S. Pat. No. 6,740,488
U.S. Pat. No. 6,740,488
U.S. Pat. No. 6,818,807
U.S. Pat. No. 6,825,400
U.S. Pat. No. 6,893,826
U.S. Pat. No. 6,900,014
U.S. Pat. No. 7,002,058
U.S. Appln. 60/685,584
U.S. Publn. 20040018518
U.S. Publn. 2006068398
Ausubel et al., In: *Current Protocols in Molecular Biology*, John, Wiley & Sons, Inc, New York, 1992.
Chen et al., *Genome Res.*, 9:492-498, 1999.
Cheng et al., *Proc. Natl. Acad. Sci. USA*, 91:5695-5699, 1994.
Coruzzi et al., EMBO J., 3:1671-1679, 1984.
Cregan et al., In: *DNA markers: Protocols, applications, and overviews*, Wiley-Liss N.Y., 173-185, 1997.
DeBlock et al., *EMBO J.*, 6:2513-2522, 1987.
Fehr, In: *Breeding Methods for Cultivar Development*, Wilcox (Ed.), Amer. Soc. of Agronomy, Madison Wis., 1987.
Haymes et al., In: *Nucleic acid hybridization, a practical approach*, IRL Press, Washington, D.C., 1985.
Innis, et al., In: *PCR Protocols. A guide to Methods and Application*, Academic Press, Inc. San Diego, 1990.
Lewin, In: *Genes V*, Oxford University Press, NY, 1994.
Nikiforov, et al. *Nucleic Acid Res.*, 22:4167-4175, 1994.
PCT Appln. WO 9200377
PCT Appln. WO/05017181
Rieger et al., In: *Glossary of Genetics: Classical and Molecular*, 5$^{th}$ Ed., Springer-Verlag: NY, 1991.
Sambrook et al., In: *Molecular cloning: a laboratory manual*, 2$^{nd}$ Ed., Cold Spring Harbor Laboratory Press, Cold Spring Harbor, N.Y., 1989.
Thompson et al., *EMBO J.* 6:2519-2523, 1987.
Toki et al., *Plant Physiol.*, 100:1503-1507, 1992.
Tyangi et al., *Nature Biotech.*, 14:303-308, 1996.
Weising et al., *Ann. Rev. Genet.*, 22:421-477, 1988.
Windels et al., *Med. Fac. Landbouww*, 64/5b:459-462, 1999.
Wingem, *Innov. Pharma. Tech.*, 00:18-24, 2000.

What is claimed:

1. A nucleic acid molecule comprising a sequence selected from the group consisting of SEQ ID NO:1, SEQ ID NO:2, SEQ ID NO:3 and SEQ ID NO:4.

2. A pair of DNA molecules, wherein a first molecule in said pair comprises at least 11 contiguous nucleotides of SEQ ID NO:3, or its full complement wherein said pair is capable of producing an amplicon diagnostic for event MON89788, wherein said amplicon comprises SEQ ID NO:1.

3. A pair of DNA molecules, wherein a first molecule in said pair comprises at least 11 contiguous nucleotides of SEQ ID NO:4, or its full complement wherein said pair is capable of producing an amplicon diagnostic for event MON89788, wherein said amplicon comprises SEQ ID NO:2.

4. A DNA detection kit specific for event MON89788 comprising:
   (a) a pair of DNA molecules, wherein a first molecule in said pair comprises at least 11 contiguous nucleotides of SEQ ID NO:3, or a sequence fully complementary thereto wherein said pair is capable of producing an amplicon diagnostic for event MON89788, wherein said amplicon comprises SEQ ID NO:1; or
   (b) a pair of DNA molecules, wherein a first molecule in said pair comprises at least 11 contiguous nucleotides of SEQ ID NO:4, or a sequence fully complementary thereto wherein said pair is capable of producing an amplicon diagnostic for event MON89788, wherein said amplicon comprises SEQ ID NO:2.

5. The nucleic acid molecule of claim 1, comprising the sequence of SEQ ID NO:1.

6. The nucleic acid molecule of claim 1, comprising the sequence of SEQ ID NO:2.

7. The DNA detection kit of claim 4, wherein the first molecule comprises at least 11 or more contiguous nucleotides of SEQ ID NO:3, or a sequence fully complementary thereto.

8. The DNA detection kit of claim 4, wherein the first molecule comprises at least 11 or more contiguous nucleotides of SEQ ID NO:4, or a sequence fully complementary thereto.

9. The nucleic acid molecule of claim 1, comprising the sequence of SEQ ID NO:3.

10. The nucleic acid molecule of claim 1, comprising the sequence of SEQ ID NO:4.

* * * * *